United States Patent
Greenawalt

(10) Patent No.: US 11,567,052 B2
(45) Date of Patent: Jan. 31, 2023

(54) NITRATE DETECTION WITH COPPER OXIDATION

(71) Applicant: Hach Company, Loveland, CO (US)

(72) Inventor: Angella Nicholle Greenawalt, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 522 days.

(21) Appl. No.: 16/667,714

(22) Filed: Oct. 29, 2019

(65) Prior Publication Data

US 2021/0123898 A1 Apr. 29, 2021

(51) Int. Cl.
G01N 33/18 (2006.01)
G01N 21/78 (2006.01)
G01N 31/22 (2006.01)

(52) U.S. Cl.
CPC ............ *G01N 33/182* (2013.01); *G01N 21/78* (2013.01); *G01N 31/227* (2013.01)

(58) Field of Classification Search
CPC ..... G01N 31/227; G01N 33/182; G01N 21/78
See application file for complete search history.

(56) References Cited

U.S. PATENT DOCUMENTS 6,039,783 A 3/2000 Lueck et al.
2018/0031535 A1 2/2018 MacFarland et al.

OTHER PUBLICATIONS

"Copper. For water, wastewater and seawater. Bicinchoninate, Porphyrin and Bathocuproine Methods," downloaded from <https://www.hach.com/asset-get.download-en.jsa?id=7639984180> on May 9, 2022. 3 pages. last modified Apr. 13, 2011. (Year: 2011).*
Green, L.C. et al. "Analysis of nitrate, nitrite, and [15N]nitrate in biological fluids," Analytical Biochemistry vol. 126, Issue 1, Oct. 1982, pp. 131-138 (Year: 1982).*
Thabano, J.R.E. et al. "Determination of nitrate by suppressed ion chromatography after copperised-cadmium column reduction," Journal of Chromatography A, 1045 (2004) 153-159 (Year: 2004).*
Dennis A. Clifford et al., "Nitrate Removal From Water Supplies by Ion Exchange", Executive Summary, Grant No. R-803898, Nov. 1977, 53 pages, University of Michigan, Ann Arbor, Michigan.

* cited by examiner

*Primary Examiner* — Jennifer Wecker
*Assistant Examiner* — Michelle Adams
(74) *Attorney, Agent, or Firm* — Ference & Associates LLC

(57) ABSTRACT

An embodiment provides a method for measuring nitrate in an aqueous sample, including: introducing an aqueous sample containing an amount of nitrate to a cation exchange resin; flowing the aqueous sample over copper metal; adding a reducing reagent to the aqueous sample; adding a colorimetric indicator to the aqueous sample; and measuring the amount of nitrate in the aqueous sample by measuring a change in intensity of the absorbance. Other aspects are described and claimed.

7 Claims, 4 Drawing Sheets

NITRATE DETECTION WITH COPPER OXIDATION

BACKGROUND

This application relates generally to measuring nitrate in aqueous or liquid samples, and, more particularly, to the measurement of nitrate using copper oxidation.

Ensuring water quality is critical in a number of industries such as pharmaceuticals and other manufacturing fields. Additionally, ensuring water quality is critical to the health and well-being of humans, animals, and plants which are reliant on the water for survival. One component of water that is typically measured is nitrate. Too much nitrate in water can be harmful to humans or animals. Therefore, detecting the presence and concentration of nitrate in water or other liquid solutions is vital.

BRIEF SUMMARY

In summary, one embodiment provides a method for measuring nitrate in an aqueous sample, comprising: introducing an aqueous sample containing an amount of nitrate to a cation exchange resin; flowing the aqueous sample over copper metal; adding a reducing reagent to the aqueous sample; adding a colorimetric indicator to the aqueous sample; and measuring the amount of nitrate in the aqueous sample by measuring a change in intensity of the absorbance.

Another embodiment provides a measurement device for measuring an amount of nitrate in a solution, comprising: a processor; and a memory storing instructions executable by the processor to: introduce an aqueous sample containing an amount of nitrate to a cation exchange resin; flow the aqueous sample over copper metal; add a reducing reagent to the aqueous sample; add a colorimetric indicator to the aqueous sample; and measure the amount of nitrate in the aqueous sample by measuring a change in intensity of the absorbance.

A further embodiment provides a method for measuring an amount of nitrate in an aqueous sample, comprising: introducing an aqueous sample containing an amount of nitrate to a cation exchange resin; flowing the aqueous sample over copper metal to produce copper(II) cations; adding a reducing reagent to the aqueous sample to reduce the copper(II) to copper(I); adding a colorimetric indicator to the aqueous sample; and measuring the amount of nitrate in the aqueous sample by measuring a change in intensity of the absorbance, wherein the absorbance intensity is correlated the amount of nitrate in the aqueous sample.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
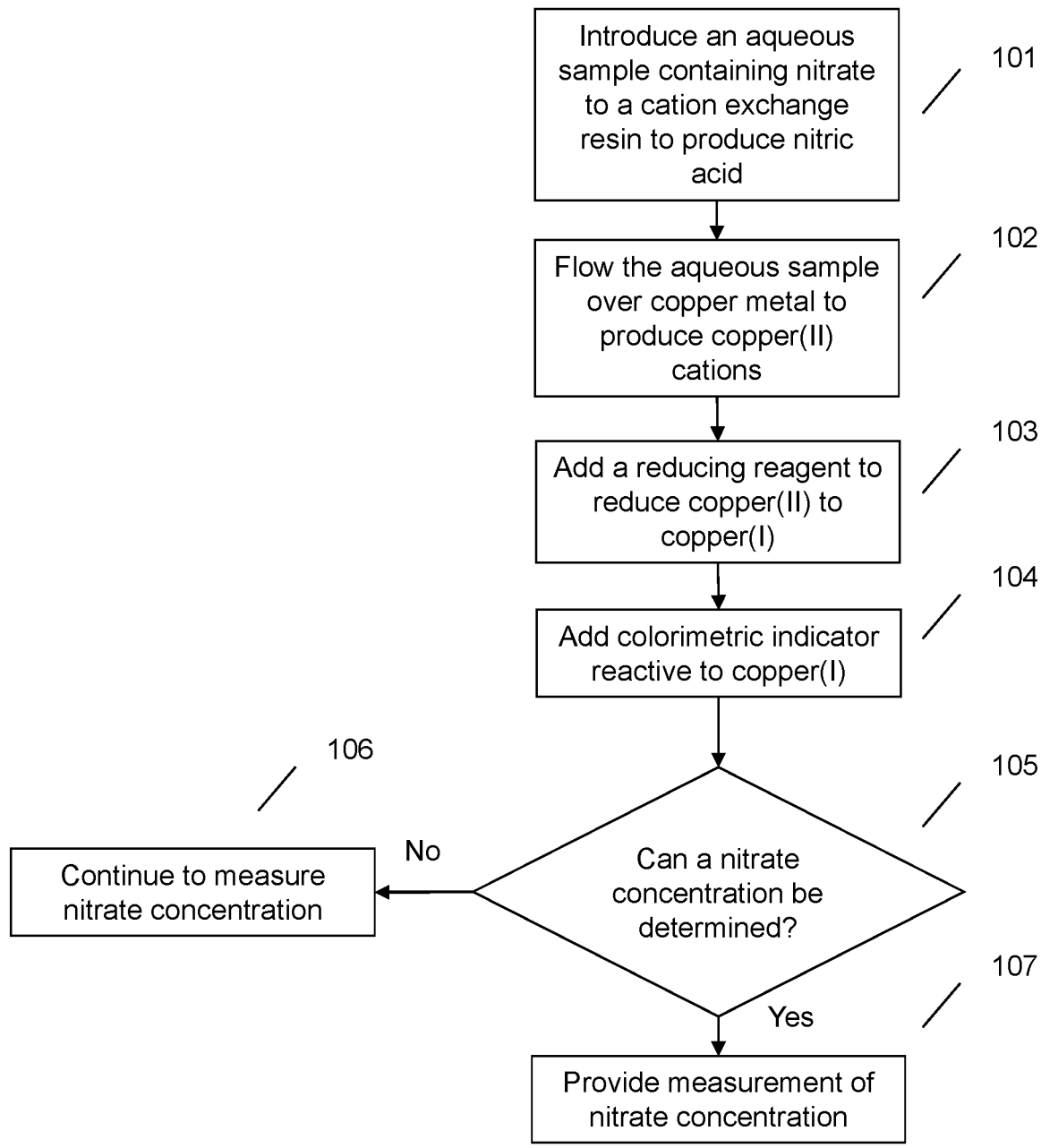
FIG. 1 illustrates a flow diagram of an example nitrate measuring system.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Conventional methods of nitrate measurement in water or an aqueous sample may have some limitations. For example, nitrate measurement may be used to determine the quality of water. High concentrations of nitrate may be harmful to animals, humans, and/or plants. Accordingly, as another example, a user or entity may want the nitrate in a body of water to be under a particular threshold, therefore, the user may measure the nitrate in order to determine if the amount of nitrate is under that threshold.

Previous methods for the measurement of nitrate have limitations. For example some methods are prone to user error. The user error may arise from improper mixing or measuring of reagents necessary to measure nitrate. Error may also be introduced from an end user improperly calibrating equipment. For example, a nitrate ion selective electrode requires proper calibration and care.

Other methods of nitrate measurement may use metal compounds. For example, cadmium metal may be used. Cadmium metal is toxic to human, animal, and plant life. Cadmium is a known carcinogen. The use of metals requires proper containment and disposal which adds to the process and cost of nitrate measurement.

Accordingly, an embodiment provides a system and method for measuring nitrate in an aqueous solution or sample. In an embodiment, an aqueous sample containing an amount of nitrate may be introduced to a cation exchange resin. The cation exchange resin may produce nitric acid.

The aqueous sample containing the nitric acid may be flowed over copper metal. The copper metal may produce copper(II) cations. In an embodiment, a reducing reagent may be added to the aqueous sample. The reducing reagent may reduce copper(II) to copper(I). In an embodiment, a colorimetric indicator may be added to the aqueous sample. The colorimetric indicator may be reactive to copper(I). The amount of nitrate in the aqueous sample may be determined by a change in intensity of absorbance of the colorimetric indicator and/or by back calculating using a transfer function (See FIG. 2).

The illustrated example embodiments will be best understood by reference to the figures. The following description is intended only by way of example, and simply illustrates certain example embodiments.

Referring to FIG. 1, an example system and method for detection of nitrate in an aqueous sample is illustrated. In an embodiment, an aqueous sample containing nitrate may be introduced to a cation exchange resin. The exchange resin may produce nitric acid. The nitric acid containing sample may be flowed over copper metal to produce copper(II) cations. The copper(II) may be reduced with a reducing agent to copper(I). A colorimetric indicator reactive to copper(I) may be added. The amount of nitrate in an aqueous sample may be determined by the absorbance change of the colorimetric indicator and/or the back calculation using a transfer function from the methods described herein.

At 101, in an embodiment, an aqueous sample may be introduced to an ion exchange resin. The aqueous sample may contain an amount of nitrate. The exchange resin may be a cation exchange resin. In an embodiment, the introduction of the aqueous sample containing an amount of nitrate to the cation exchange resin may produce nitric acid. In an embodiment, the nitric acid may be in a dilute concentration. In an embodiment, the exchange resin may exchange particular ions in a solution that passes through the resin. In an embodiment the cation exchange resin takes an aqueous sample containing an amount of nitrate and after passing through the resin produces nitric acid (see FIG. 2). The nitric acid may be dilute. The exchange resin may be reusable. The exchange resin may be reused for multiple uses without any maintenance, or alternatively, the resin may be reconditioned for further use. The cation exchange resin may be a standalone step, part of an apparatus to direct effluent to another step of the method, or the like.

The aqueous sample may be an aqueous sample which may include a sample from a natural body of water, a holding tank, a processing tank, a pipe, or the like. The aqueous sample may be in a continuous flow, a standing volume of liquid, or any combination thereof. In one embodiment, the solution may be introduced to one or more chambers or vessels, for example, a test chamber of the measurement device. In an embodiment, the measurement device may be a hand held device. A hand held device may have advantages such as lower cost, portability, field use, or the like. Alternatively, the measurement device may be a larger bench top device. Introduction of the aqueous sample into the measurement device may include placing or introducing the solution into a test chamber manually by a user or using a mechanical means, for example, gravity flow, a pump, pressure, fluid flow, or the like. For example, a water sample for measurement may be introduced to a measurement or test chamber using a pump. In an embodiment, valves or the like may control the influx and efflux of the solution into or out of the one or more chambers, if present.

Additionally or alternatively, the measurement device may be present or introduced in a volume of the aqueous sample. The measurement device is then exposed to the volume of aqueous sample where it may perform measurements. The system may be a flow-through system in which a solution and/or reagents are automatically mixed and measured. Once the sample is in contact with the measurement system, the system may measure the nitrate of the sample, as discussed in further detail herein. In an embodiment, the measurement device may include one or more chambers in which the one or more method steps may be performed.

At 102, in an embodiment, the aqueous sample may be flowed over copper metal. In an embodiment, the flowing over copper of the aqueous sample may be performed after the introduction of the aqueous sample to the cation exchange resin. The copper metal may be in any form. For example, the copper metal may be in a solid form as either small shavings or larger pieces, impregnated upon a media, or the like. In an embodiment, the flowing of the aqueous sample over copper metal may produce copper(II) cations. In an embodiment, the nitric acid produced as a result of the nitrate within the sample reacting with the cation exchange resin reacts with the copper metal to form copper(II) cations (see FIG. 2). The flowing may be over the copper metal, through the copper metal, in any manner that provides sufficient contact of the aqueous sample to the copper metal, or the like. The copper metal may be reusable for multiple reactions. However, the longevity of the copper metal may be determined by factors such as the concentration of the nitric acid, an aqueous sample flow rate, an aqueous sample flow volume, size of the copper metal material, or the like. The copper may be contained in a chamber or vessel. The copper metal chamber or vessel may be serviceable for copper metal replacement or disposable to be discarded at the end of use.

At 103, in an embodiment, a reducing reagent may be added to the aqueous sample. In an embodiment, the reducing reagent may reduce copper(II) to copper(I) (see FIG. 2). In an embodiment, the reducing agent may be added after the flowing of the aqueous sample over copper metal. The reducing agent may be contained in a powder pillow. The reducing agent may be in a powder pillow with a colorimetric indicator. In an embodiment, the powder pillow may be the Hach® CuVer 2™ powder pillow. Other methods to introduce the reducing reagent are contemplated and disclosed. For example, a reducing reagent may be added using a dropper, pipette, controlled flow system, as a solid, or the like. Specific examples are for example embodiments, and are not intended to be limiting.

At 104, in an embodiment, a colorimetric indicator may be added to the aqueous sample. In an embodiment, the colorimetric indicator may give a measurable parameter, such as color or absorbance, to the amount of nitrate in the aqueous sample. (see FIG. 2). In an embodiment, the colorimetric indicator may be sensitive to the reduced copper produced by the reducing agent. In an embodiment, the colorimetric indicator may be added after the flowing of the aqueous sample over copper metal and reaction with the added reducing agent. The colorimetric indicator may be contained in a powder pillow. The colorimetric indicator may be in a powder pillow with a reducing reagent. In an embodiment, the powder pillow may be the Hach® CuVer 2™ powder pillow. Other methods to introduce the colorimetric indicator are contemplated and disclosed. For example, a reducing reagent may be added using a dropper, pipette, controlled flow system, as a solid, or the like. Specific examples are for example embodiments.

Figure 3:
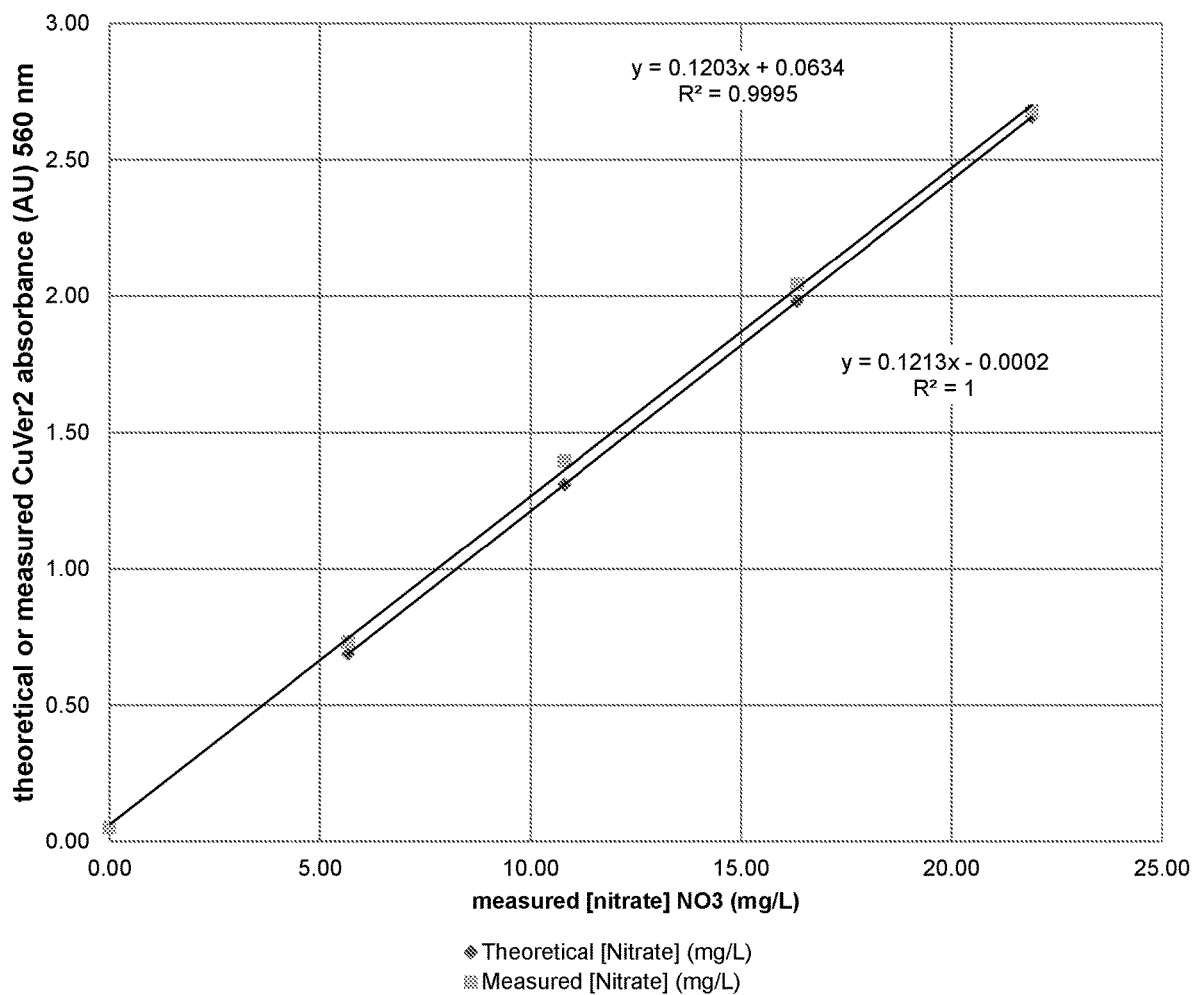
FIG. 3 illustrates a response of a current Nitrate Ion Selective Electrode compared to an embodiment of the nitrate detection method using the colorimetric Hach® CuVer 2™ Powder Pillow measuring an amount of copper in a solution.

At 105, in an embodiment, the system and method may determine if an amount of nitrate in an aqueous sample may be measured. In an embodiment, the presence of an amount of nitrate in an aqueous sample may cause an increase in absorbance intensity of the colorimetric indicator. In an embodiment, the colorimetric indicator may be reactive for copper(I). In an embodiment, the copper(I) may be produced by exposing the aqueous sample containing the copper(II) cations to a reducing agent. Examples of this increase in absorbance intensity and dose response curves for a colorimetric indicator may be illustrated in FIG. 3. Therefore, the absorbance intensity, of an aqueous sample containing nitrate may be correlated to the concentration of the nitrate in the aqueous sample. Absorbance curves may be generated for a range of nitrate concentrations, for different colorimetric indicators, for any different condition that may affect absorption (e.g., temperature, sample content, turbidity, viscosity, measurement apparatus, aqueous sample chamber, etc.), or the like.

Figure 2:
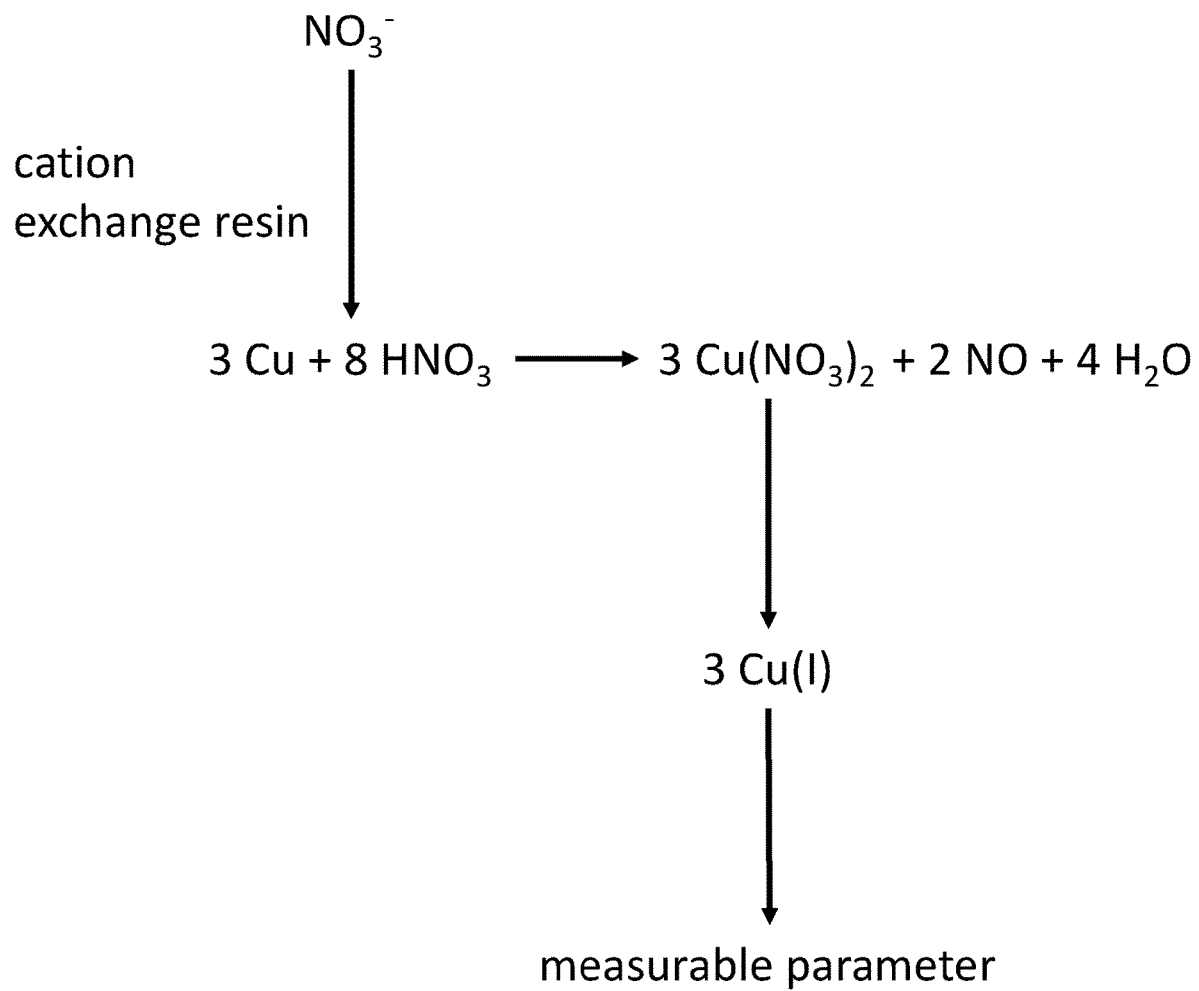
FIG. 2 illustrates a transfer function for detection of nitrate in an embodiment.

Alternatively or additionally, the amount of nitrate in an aqueous sample may be determined by back calculating using the chemical equations illustrated in FIG. 2. For example, a colorimetric change occurs from reaction of copper(I). The copper(I) may have been produced from the reduction of copper(II) using a reducing agent. The copper (II) cations may have been produced by flowing an aqueous sample containing nitric acid over copper metal. The nitric acid may have been produced by exposing an aqueous sample containing nitrate to a cation exchange resin. These chemical reactions may have known reactants and stoichiometry. Therefore, a colorimetric indicator and the associated absorbance intensity may be correlated to the amount of nitrate in an aqueous sample.

Alternatively or additionally, nitrate concentration measurement may be at periodic intervals set by the user or preprogrammed frequencies in the device. Measurement of nitrate by a device allows for real time data with very little human involvement in the measurement process. Cleaning of the absorbance chamber may be required at an unspecified time interval. A programmed calibration curve may be entered into the device.

A chamber, vessel, cell, chamber, or the like may contain an aqueous sample, at least one colorimetric indicator, and associated reagents such as buffers and/or additives. A device may contain one or more bottles of reagents which contain necessary reagents. The reagents contained in the one or more bottles may be pump fed or gravity fed. The flow of the reagents may be metered to ensure proper volume delivery to the measurement cell. The aqueous sample may be fed through a pressured inlet, a vessel, or the like. The aqueous sample may be introduced into the measurement chamber by a pump or gravity fed. The sampling device may be in series or parallel to an aqueous flow. The device may have a system to ensure proper mixing of the aqueous sample, colorimetric indicator, and related reagents.

The absorbance intensity or nitrate concentration may be an output upon a device in the form of a display, printing, storage, audio, haptic feedback, or the like. Alternatively or additionally, the output may be sent to another device through wired, wireless, fiber optic, Bluetooth®, near field communication, or the like. An embodiment may use an alarm to warn of a measurement or concentration outside acceptable levels. An embodiment may use a system to shut down water output or shunt water from sources with unacceptable levels of nitrate. For example, a nitrate measuring device may use a relay coupled to an electrically actuated valve, or the like.

At 106, in an embodiment, if an amount of nitrate cannot be determined, the system may continue to measure nitrate. Additionally or alternatively, the system may output an alarm, log an event, or the like.

At 107, in an embodiment, if an amount of nitrate can be determined, the system may provide a measurement of nitrate concentration. The system may connect to a communication network. The system may alert a user or a network. This alert may occur whether an amount of nitrate measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if an amount of nitrate concentration reaches a threshold. Alarms or logs may be analyzed in real-time, stored for later use, or any combination thereof.

The various embodiments described herein thus represent a technical improvement to conventional nitrate measurement techniques. Using the techniques as described herein, an embodiment may use a method to determine an amount of nitrate in an aqueous sample. This is in contrast to conventional methods with limitations mentioned above. Such techniques provide a faster and more accurate method for measuring nitrate in an aqueous or liquid solution.

Figure 4:
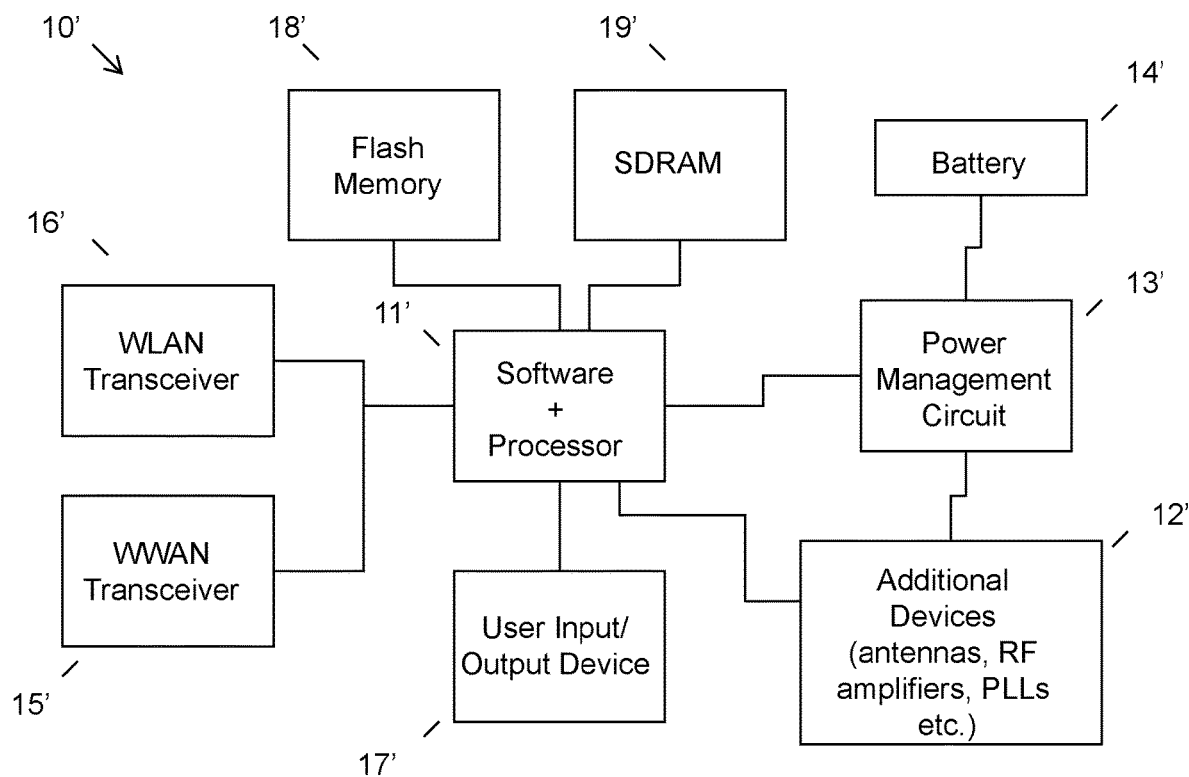
FIG. 4 illustrates an example of computer circuitry.

While various other circuits, circuitry or components may be utilized in information handling devices, with regard to an instrument for measurement of nitrate according to any one of the various embodiments described herein, an example is illustrated in FIG. 4. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform measurement of nitrate of an aqueous sample.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring an amount of nitrate in an aqueous sample, comprising:
   introducing an aqueous sample containing an amount of nitrate to a cation exchange resin;
   flowing the aqueous sample over copper metal to produce copper(II) cations;
   adding a reducing reagent to the aqueous sample to reduce the copper(II) cations to copper(I);
   adding a colorimetric indicator to the aqueous sample; and
   measuring the amount of nitrate in the aqueous sample by measuring an absorbance intensity.

2. The method of claim 1, wherein the introducing the aqueous sample to the cation exchange resin produces nitric acid.

3. The method of claim 1, wherein at least one of the reducing reagent and the colorimetric indicator are introduced to the aqueous sample via a powder pillow.

4. The method of claim 1, wherein the colorimetric indicator is reactive to copper(I).

5. The method of claim 1, wherein the amount of nitrate is determined based on one or more chemical reactions.

6. The method of claim 1, wherein the absorbance intensity is correlated to a concentration of the nitrate in the solution based on a calibration curve.

7. The method of claim 1, wherein the aqueous sample comprises a water sample for quality testing.

* * * * *